United States Patent [19]
Darnley

[11] Patent Number: 5,484,204
[45] Date of Patent: Jan. 16, 1996

[54] MECHANICAL COOLING SYSTEM

[75] Inventor: Robert L. Darnley, Collingswood, N.J.

[73] Assignee: TA Instruments, Inc., New Castle, Del.

[21] Appl. No.: 309,769

[22] Filed: Sep. 21, 1994

[51] Int. Cl.$^6$ .......................... G01N 25/00; G01K 17/00; F25B 39/02
[52] U.S. Cl. ........................ 374/10; 374/31; 374/208; 62/331; 62/518
[58] Field of Search ..................... 374/10, 11, 12, 374/31, 33, 208, 120; 62/516, 518, 331, 499; 165/169

[56] References Cited

U.S. PATENT DOCUMENTS

| | | | |
|---|---|---|---|
| 2,391,876 | 1/1946 | Brown | 165/169 |
| 3,379,061 | 4/1968 | Mercier | 374/33 |
| 3,456,490 | 7/1969 | Stone . | |
| 4,154,085 | 5/1979 | Hentze | 374/10 |
| 4,979,896 | 12/1990 | Kinoshita . | |
| 5,098,196 | 3/1992 | O'Neill . | |
| 5,193,910 | 3/1993 | Kinoshita . | |
| 5,211,477 | 5/1993 | Li . | |
| 5,439,291 | 8/1995 | Reading | 374/11 |

FOREIGN PATENT DOCUMENTS

| | | | |
|---|---|---|---|
| 947655 | 7/1982 | U.S.S.R. . | |
| 1054689 | 11/1983 | U.S.S.R. | 374/31 |
| 865073 | 4/1961 | United Kingdom | 374/11 |

OTHER PUBLICATIONS

"Mechanical Cooling Accessory"–TA Instruments Product Brochure.

*Primary Examiner*—William A. Cuchlinski, Jr.
*Assistant Examiner*—Andrew Hirshfeld
*Attorney, Agent, or Firm*—Crowell & Moring

[57] ABSTRACT

The present invention is a mechanical cooling system, for use with thermal analysis instruments such as differential scanning calorimeters, which interposes a gaseous heat transfer path between the heat exchanger or evaporator cooling the differential scanning calorimeter cell and the differential scanning calorimeter cell. This configuration improves the performance of the thermal analysis system by reducing noise in the heat flow signal otherwise resulting from evaporation of the refrigerant in the heat exchanger. The mechanical cooling system is attached to the thermal analysis instrument by an arrangement providing for minimum direct physical contact between the mechanical cooling system and the thermal analysis instrument.

36 Claims, 4 Drawing Sheets

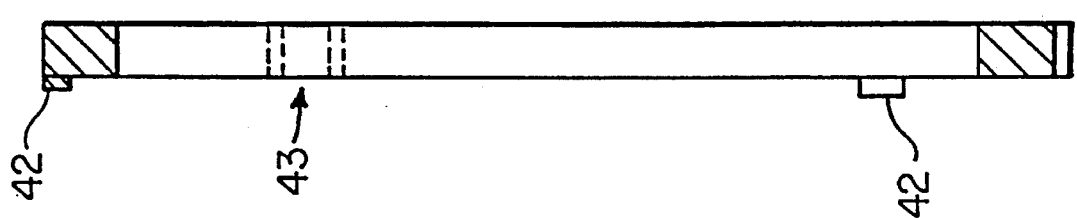
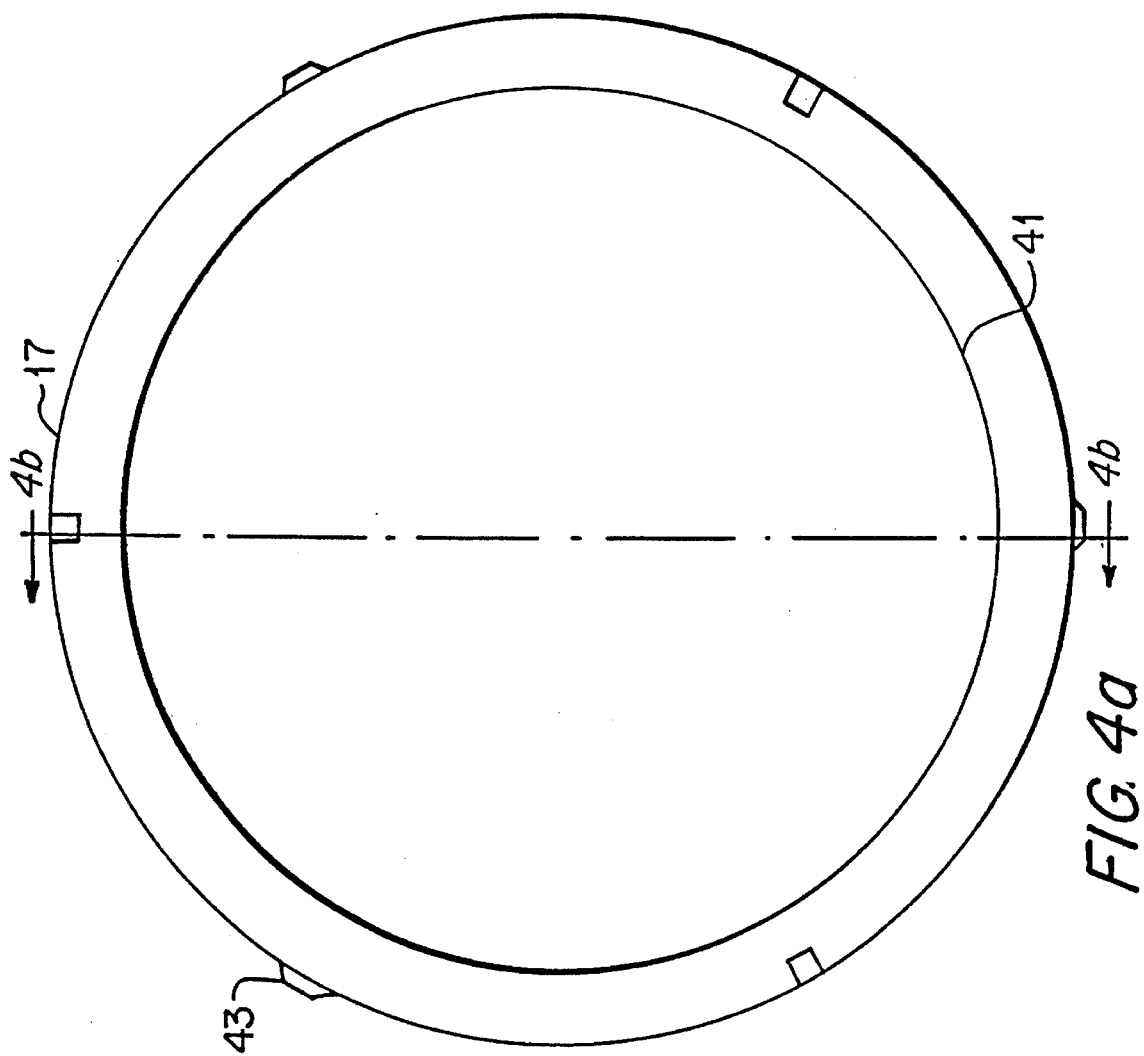

MECHANICAL COOLING SYSTEM

BACKGROUND

1. Field of the Invention

This invention relates to closed-cycle mechanical cooling systems used with thermal analysis instruments such as differential scanning calorimeters ("DSCs") to control the temperature of a sample undergoing analysis.

2. Background

Mechanical Cooling Accessories (MCAs) have been sold for many years, for use with Differential Scanning Calorimeters. The MCAs allow operation of DSCs in the temperature range of −70° C. to 350° C. The MCAs are economical and convenient to use because they do not use expendable coolants such as liquid nitrogen, as do other types of cooling systems for DSCs. However, prior art MCAs have not been very successful commercially, because they cause a large increase in baseline heat flow noise. Prior art MCAs also suffer from problems caused by condensation and subsequent frost build-up on the exterior of the MCA's cooling head assembly.

An example of a cooling head for a prior art MCA is shown in FIG. 1. The prior an MCA is a two stage vapor compression refrigeration system. It is specially designed to mate with a DSC cell. The cooling head comprises a hollow copper cylinder 1, with a hollow stainless steel cylinder 2 brazed to the top of copper cylinder 1. Stainless steel cylinder 2 has an annular cavity 3. Liquid refrigerant (such as ethane) is fed into this cavity where it evaporates, thus extracting heat from the evaporator formed by copper cylinder 1 and stainless steel cylinder 2. Copper cylinder 1 is in direct physical and thermal contact with the top surface 4 of the DSC cell. Heat flows from the top of the cell to blocks 1 and 2, and is removed by the evaporating refrigerant. One or two insulating rings 5 of polyamide plastic, approximately 0.005" thick are inserted in the heat flow path between the DSC cell and copper cylinder 1 to limit the heat flow from the DSC cell. Insulating rings 5 are necessary to reduce the cooling effect such that the DSC cell can reach a temperature of 350° C., and to reduce thermal noise in the DSC heat flow signal. The evaporator is enclosed in a housing 6 which is filled with thermal insulation 7.

Thermal noise in the DSC heat flow signal is produced by fluctuations in the evaporator temperature, caused by evaporation of the liquid refrigerant. In the prior art MCA, the fluctuations in the evaporator temperature are very irregular. The fluctuations cause changes in the heating rate of the DSC cell, which causes variations in heat flow to and from the DSC cell, thus producing noise in the heat flow signal.

SUMMARY OF THE INVENTION

The present invention is shown schematically in FIG. 2. Instead of using a heat flow path that relies on strong heat transfer over a relatively small area, as in the prior art MCA shown in FIG. 1, the present invention uses a heat flow path with a much weaker heat transfer distributed over a much larger area. The cooling head of the present invention provides the same total cooling power as the prior art cooling head, but with much less heat flow noise.

In the present invention, direct contact between the evaporator and the DSC cell is completely eliminated. Heat is transferred from the DSC cell to the evaporator through a layer of gas that separates the evaporator and the DSC cell (both laterally and vertically). Because this heat transfer mode is much weaker than the direct contact heat transfer used in the prior art MCA, a much larger heat transfer area is required than the area of the top of the DSC cell. In the present invention, the evaporator surrounds the DSC cell, such that heat is transferred through the lateral surface of the DSC cell, as well as through the top surface of the DSC cell.

The gap between the DSC cell and the evaporator is, e.g., 0.020" to 0.060", preferably 0.040", both at the top of the cell and at the lateral surfaces. The strength of the heat transfer between the cell and the evaporator depends on the size of the gap and the thermal conductivity of the gas filling the gap. If the gap is not uniform, there will be stronger heat transfer where the gap is smallest and weaker heat transfer where it is larger. Any non-uniformity of the gap would cause asymmetrical flow of heat from the DSC cell to the evaporator, and would produce on offset in the baseline heat flow to or from the DSC cell.

Although baseline offsets can generally be compensated for, if the uniformity of the gap varies during a DSC run the resulting variation of the baseline heat flow will likely be so unpredictable that compensation would be impossible. Accordingly, it is essential that the gap between the evaporator and the DSC cell be as uniform as possible, and that it remains uniform for sufficiently long periods such that the DSC can be calibrated at reasonable intervals. However, periodic recalibration of the DSC will generally be necessary.

By changing the composition of the gas in the gap between the DSC cell and the evaporator, the heat transfer between the DSC and evaporator can be controlled. Because increased heat transfer leads to an increase in baseline noise, the user can choose between a high heat transfer rate for greater cooling power, and a lower heat transfer rate for low-noise operation. The user can use a mixture of heat transfer gases, such as helium and nitrogen, which have very different thermal conductivities. Pure helium can be used for higher heat transfer, pure nitrogen for lower heat transfer, and mixtures of helium and nitrogen to obtain moderate rates of heat transfer. Other gases can also be used. For example, argon has a lower thermal conductivity than nitrogen, and hydrogen has a higher thermal conductivity than helium. Pure helium or hydrogen may be used in the gap during cooling, increasing cooling rates but also increasing noise somewhat. Then, during heating when less cooling is required, a lower thermal conductivity gas such as nitrogen or argon could be used, decreasing the cooling effect and the heat flow noise.

Accordingly, the present invention is a two-stage mechanical refrigeration system. The cooling head assembly includes an evaporator which surrounds the DSC cell, but is not in direct physical or thermal contact with the DSC cell. Heat transfer between the evaporator and the DSC cell is limited, as much as possible, to transfer heat via gases such as helium and/or nitrogen. The gap between the evaporator and the DSC cell is uniform.

BRIEF DESCRIPTION OF THE DRAWINGS

FIGS. 3a and 3b are schematic diagrams of a top view and a cross section, respectively, of the evaporator support ring. The cross-section of FIG. 3b is taken along line 3b—3b of FIG. 3a.

FIGS. 4a and 4b are schematic diagrams of a top view and a cross section, respectively, of the flange which is mounted on the DSC housing. The cross-section of FIG. 4b is taken along line 4b—4b of FIG. 4a.

DETAILED DESCRIPTION OF THE INVENTION

Figure 1:
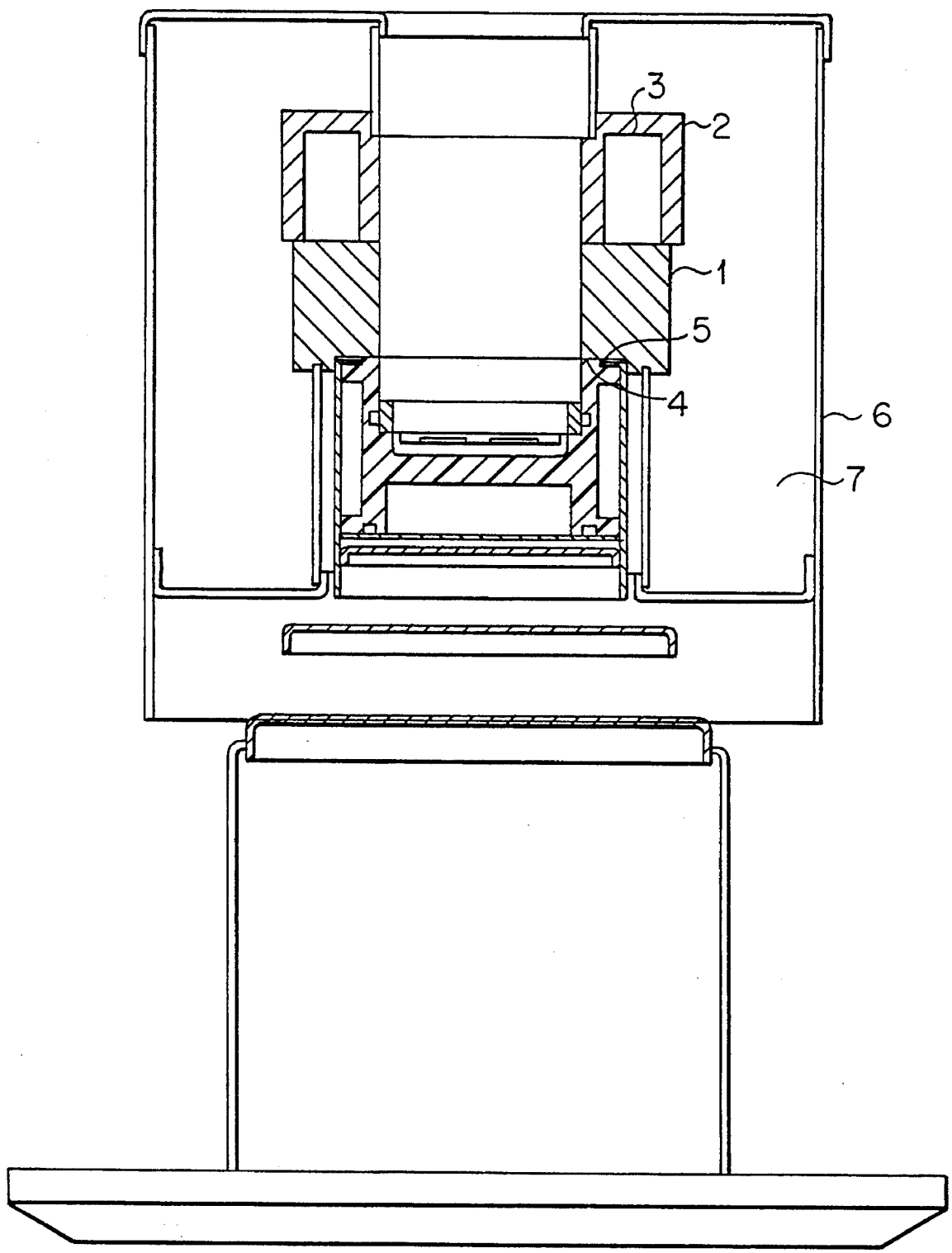
FIG. 1 is a schematic diagram of a prior art mechanical cooling accessory.
Figure 2:
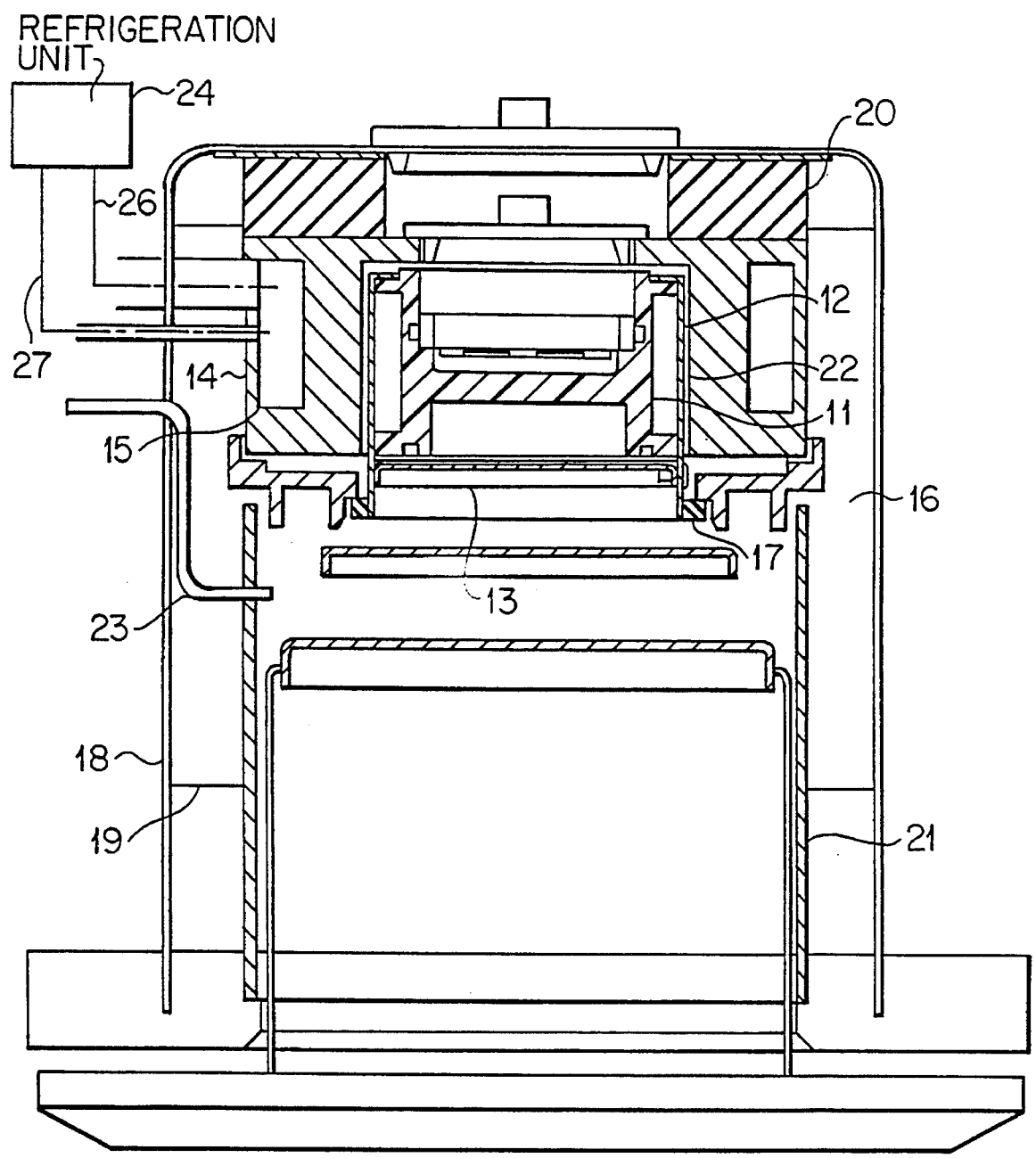
FIG. 2 is a schematic diagram of the present invention.

FIG. 2 shows a DSC cell 11 surrounded by a thin sheet metal (e.g., nickel) housing 12, which covers the lateral surface of cell 11 and attaches cell 11 to support 13. Heat is transferred from the DSC cell to evaporator 14, which completely surrounds the cell. Evaporator 14 is a hollow copper cylinder with a thick wall. Subcooled liquid refrigerant is supplied to cavity 15 in evaporator 14 via tube 27. Evaporation of the refrigerant in cavity 15 cools evaporator 14. Evaporator 14 is supported and positioned by stainless steel evaporator ring 16, which is itself supported and positioned by stainless steel flange 17. Evaporated refrigerant is removed via tube 26, and returned to refrigeration unit 24 for condensation. Flange 17 is attached to housing 12. Thus the only direct physical contact between evaporator 14 and DSC cell 11 is through flange 17, as described below.

Evaporator ring 16 is close fit to both evaporator 14 and flange 17, so that the position of the evaporator relative to the DSC cell housing is accurately controlled. The direct physical contact between evaporator ring 16 and evaporator 14 is at four small contact regions, spaced around the evaporator. Three, five or six contact regions could also be used. Each of the contact regions includes a vertical and a horizontal surface to center and support the evaporator. The small contact areas limit the flow of heat between the evaporator and evaporator ring, by reducing heat transfer via direct physical contact. Similarly, the direct physical contact between evaporator ring 16 and flange 17 consists of six small contact regions. Three of these contact regions are in the horizontal plane to support the evaporator ring on the housing flange, and three are positioned about the outside diameter of the flange 17 to center evaporator ring 16 on flange 17. Evaporator ring 16 is preferably made of a low thermal conductivity material, such as stainless steel which can withstand the temperature range, e.g., −70 ° C. to 350 ° C., of the DSC operation.

The evaporator and its support system is enclosed by an aluminum housing 18 which has an electric resistance heater 19 on its inner surface. Heater 19 maintains the housing at a constant temperature above ambient to prevent condensation of moisture on the exterior of the housing.

A sponge rubber ring 20 is positioned between the evaporator and the inside top of housing 18, such that when the cooling head is installed on the DSC cell, ring 20 is compressed, holding evaporator 14 in position on DSC cell 11. Cylinder 21 supports evaporator ring 16 when the cooling head assembly is removed, such that the cooling accessory can be removed as an assembly. The space between housing 18 and evaporator 14, evaporator ring 16, cylinder 21 and sponge rubber ring 20 is filled with thermal insulation, such as alumino-silicates to limit the flow of heat from housing 18 to evaporator 14.

This mounting system accurately maintains the relative position of the evaporator and the DSC cell, while reducing direct physical contact heat transfer to a minimum. This structure ensures that heat transfer is almost entirely through the gas in cavity 22 between evaporator 14 and DSC cell 11. Heat transfer takes place over the entire outer surface of DSC cell housing 12, thus meeting the requirement of a low heat transfer over a large area. The DSC cell is typically purged with a small flow of an inert gas, such as nitrogen. A heat transfer gas, typically helium, nitrogen, or a combination of helium and nitrogen, as discussed above, is supplied to the interior cavity 22 via tube 23.

Figure 3B:
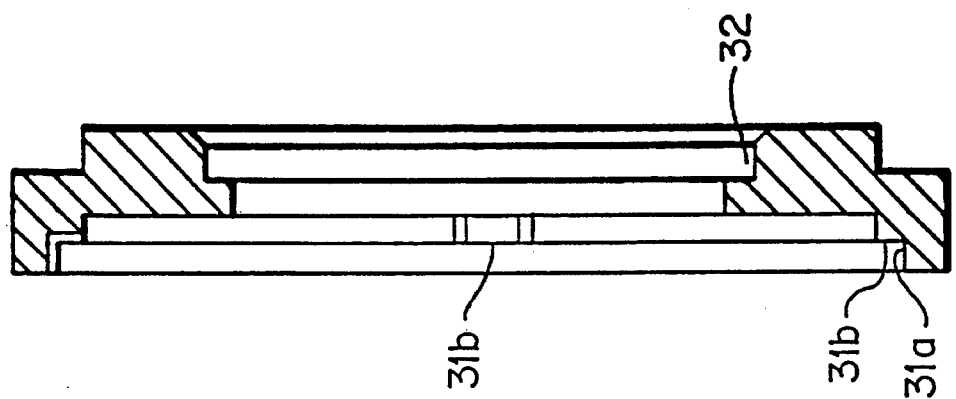
Figure 3A:
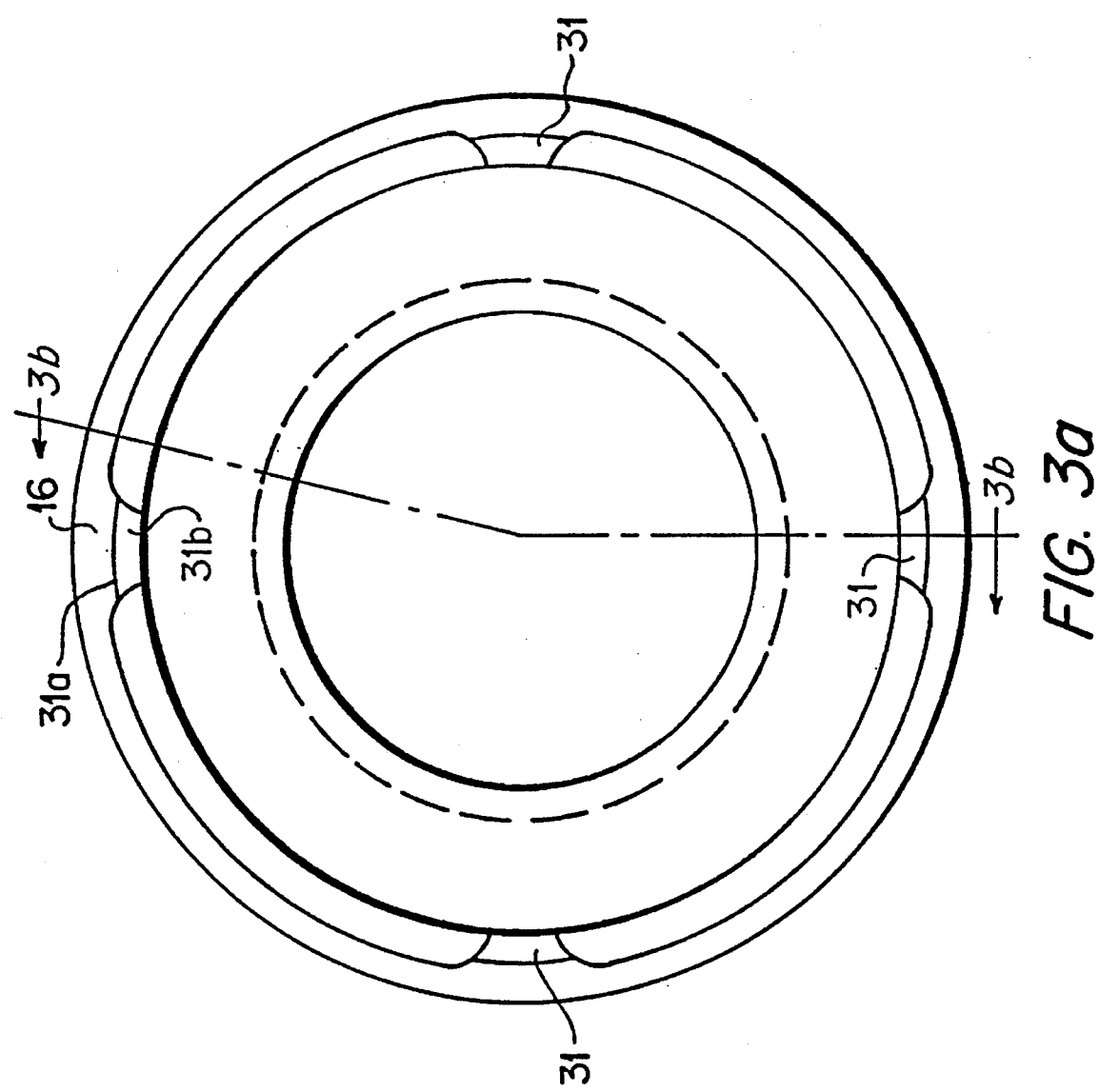

FIGS. 3a and 3b are schematic diagrams of evaporator support ring 16, shown in a top view and in a cross-section, respectively. The surfaces which contact the evaporator are formed by counterboring a cavity in the top surface of evaporator ring 16 and removing most of the bottom and side surfaces of that counterbore, leaving just four small contact regions 31. Regions 31 consist of regions 31a which are the remaining portions of the cylindrical surface of the original counterbore, and regions 31b which are the remaining portions of the flat bottom surface of the original counterbore. The evaporator is supported and accurately positioned only by the four contact regions 31. The opposite side of evaporator ring 16 (the underside) has a counterbore 32, which engages the flange on the DSC cell housing.

FIGS. 4a and 4b show the configuration of flange 17, which is mounted on DSC cell housing 12. Flange 17 has an inner bore 41, which is attached to DSC cell housing 12 by brazing. Almost all the top surface of the flange is removed by machining, such that only three small rectangular flat surfaces 42 remain. The outside diameter of flange 17 is also removed by machining, such that only three small curved surfaces 43 remain. Surfaces 42 and 43 engage the bottom and the side, respectively, of the counterbore in the underside of evaporator ring 16.

Although the primary purpose of the present invention is to improve the operation of DSC when using a closed cycle vapor compression refrigeration system, the present invention can also be used with different types of cooling systems. For example, DSCs are often cooled using expendable coolants which remove heat by change of phase, such as liquid nitrogen or other liquid cryogens. In that application, the liquid cryogen is fed to the evaporator in the same way that the refrigerant in the closed cycle refrigeration system is fed to the evaporator, but the vapor produced by the phase change is discharged to the environment upon leaving the evaporator, instead of being recycled. Alternatively, thick-walled cylinder 14 may be used as a heat exchanger instead of as an evaporator. In that case, thick-walled cylinder 14 would have the same structure as shown in FIG. 2, but liquid coolant would be pumped back for refrigeration, instead of vapor coolant. Alternatively, the cold vapor boiled off liquid nitrogen could be passed through the heat exchanger, cooling the DSC by absorbing heat from the warmer surroundings. In this manner, the present invention may be used to cool the DSC by single phase heat transfer from either liquid or vapor-phase coolants.

As used herein, a minimum contact support structure is a support structure which reduces the direct physical contact (to the component it supports) to the minimum direct physical contact required to support and position the component. As used herein, "heat exchanger" shall include evaporators as well as heat exchangers in which the coolant does not change phase.

The foregoing disclosure of embodiments of the present invention has been presented for purposes of illustration and description. It is not intended to be exhaustive or to limit the invention to the precise forms disclosed. Many variations and modifications of the embodiments described herein will be obvious to one of ordinary skill in the art in light of the above disclosure. The scope of the invention is to be defined only by the claims appended hereto, and by their equivalents.

What is claimed is:

1. A cooling head for a differential scanning calorimeter cell comprising:
   (a) an evaporator comprising a thick-walled cylinder, said cylinder having a first annular cavity therein;
   (b) an evaporator ring supporting and positioning the evaporator with a minimum contact structure;
   (c) a flange having an inner bore, said inner bore being attached to the differential scanning calorimeter cell, and said flange engaging the evaporator ring with a minimum contact structure; and
   (d) means for introducing a liquid refrigerant into the first annular cavity, and means for removing evaporated refrigerant from the first annular cavity.

2. The cooling head of claim 1, wherein the differential scanning calorimeter cell has an outer diameter, and the inner diameter of the thick-walled cylinder is selected to be greater than the outer diameter of the differential scanning calorimeter cell, such that when the evaporator is mounted around the differential scanning calorimeter cell, a second cavity is formed between the outer surface of the differential scanning calorimeter cell and the inner surface of the evaporator.

3. The cooling head of claim 2, further comprising means for introducing a heat transfer gas into the second cavity.

4. The cooling head of claim 3, wherein the means for introducing a heat transfer gas into the second cavity comprises means for introducing a heat transfer gas which is a composition of at least two gases.

5. The cooling head of claim 2, wherein the evaporator ring is close fit to the evaporator, and the flange is close fit to the evaporator ring.

6. The cooling head of claim 2, wherein the outer diameter of the second cavity is greater than the inner diameter of the second cavity by 0.020 to 0.060 inches.

7. The cooling head of claim 1, wherein the minimum contact structure between the evaporator ring and the evaporator consists of three to six contact regions.

8. The cooling head of claim 1, wherein the flange engages the evaporator ring at three contact regions on the top of the flange and at three contact regions on the outside diameter of the flange.

9. The cooling head of claim 1, further comprising an outer housing surrounding the evaporator, wherein a space between the outer surface of the evaporator and the housing is substantially filled with an insulation material.

10. The cooling head of claim 9, further comprising an electrical resistance heater attached to the inner surface of the outer housing.

11. A differential scanning calorimeter comprising:
    (a) a differential scanning calorimeter cell having an outer surface;
    (b) an evaporator comprising a thick-walled cylinder having a first annular cavity therein, said thick-walled cylinder having an inner surface;
    (c) an evaporator ring supporting and positioning the evaporator with a minimum contact structure;
    (d) a flange attached to the differential scanning calorimeter cell and engaging the evaporator ring with a minimum contact structure; and
    (e) means for introducing liquid refrigerant into the first cavity, and means for removing evaporated refrigerant from the first cavity,
    wherein the evaporator surrounds the differential scanning calorimeter cell, such that a second cavity is formed between the outer surface of the differential scanning calorimeter cell and the inner surface of the thick-walled cylinder.

12. The differential scanning calorimeter of claim 11, further comprising means for introducing a heat transfer gas into the second cavity.

13. The differential scanning calorimeter of claim 12, wherein the means for introducing a heat transfer gas into the second cavity comprises means for introducing a mixture of nitrogen and helium as the heat transfer gas.

14. The differential scanning calorimeter of claim 11, wherein the second cavity is 0.020 to 0.060 inches wide.

15. The differential scanning calorimeter of claim 11, further comprising an outer housing surrounding the evaporator, wherein a space between the outer surface of the evaporator and the housing contains an insulation material.

16. The differential scanning calorimeter of claim 15, further comprising an electrical resistance heater attached to the inner surface of the outer housing.

17. The differential scanning calorimeter of claim 15, further comprising a sponge rubber ring positioned between the evaporator and the inside of the top of the outer housing.

18. The differential scanning calorimeter of claim 11, wherein the minimum contact structure between the evaporator ring and the evaporator consists of three to six contact regions.

19. The differential scanning calorimeter of claim 11, wherein the minimum contact structure between the flange and the evaporator ring consists of three contact regions at the top of the flange and three contact regions on the outside diameter of the flange.

20. A method for cooling a differential scanning calorimeter cell comprising:
    (a) providing a cooling head comprising an evaporator having a thick-walled cylinder with a first annular cavity therein, and an evaporator ring supporting and positioning the evaporator, and also providing a flange attached to the differential scanning calorimeter cell, said flange configured to engage the evaporator ring with a minimum contact structure;
    (b) forming a second cavity between the outer surface of the differential scanning calorimeter cell and the inner surface of the thick-walled cylinder by installing the cooling head over the differential scanning calorimeter cell and engaging the evaporator ring with the flange;
    (c) introducing a heat transfer gas into the second cavity and a liquid refrigerant into the first cavity, such that evaporation of the liquid refrigerant in the first cavity cools the evaporator, and heat is transferred from the differential scanning calorimeter cell to the evaporator by the heat transfer gas; and
    (d) removing evaporated refrigerant from the first cavity, and condensing the evaporated refrigerant.

21. The method of claim 20, wherein the heat transfer gas is a mixture of two gases, the first gas having a significantly higher thermal conductivity than the second gas.

22. The method of claim 21, wherein the first gas is helium.

23. The method of claim 22, wherein the second gas is nitrogen.

24. The method of claim 21, further comprising cooling the differential scanning calorimeter cell to a first temperature using the heat transfer gas, wherein the heat transfer gas primarily comprises the first gas.

25. The method of claim 24, further comprising heating the differential scanning calorimeter cell from the first temperature using the heat transfer gas wherein the heat transfer gas comprises a substantial proportion of the second gas.

26. The method of claim 25, further comprising increasing the proportion of the second gas in the heat transfer gas in temperature regions wherein a low noise heat flow signal is desired.

27. A cooling head for a differential scanning calorimeter cell comprising:

(a) a heat exchanger comprising a thick-walled cylinder, said cylinder having at least one cooling cavity therein;

(b) a heat exchanger support ring supporting and positioning the heat exhanger with a minimum contact structure;

(c) a flange having an inner bore, said inner bore being attached to the differential scanning calorimeter cell, and said flange engaging the heat exchanger support ring with a minimum contact structure; and (d) means for passing a refrigerant through the at least one cooling cavity.

28. The cooling head of claim 27, wherein the differential scanning calorimeter cell has an outer diameter, and the inner diameter of the thick-walled cylinder is selected to be greater than the outer diameter of the differential scanning calorimeter cell, such that when the heat exchanger is mounted around the differential scanning calorimeter cell, a heat transfer cavity is formed between the outer surface of the differential scanning calorimeter cell and the inner surface of the heat exchanger.

29. The cooling head of claim 28, further comprising means for introducing a heat transfer gas into the heat transfer cavity.

30. The cooling head of claim 29, wherein the means for introducing a heat transfer gas into the heat transfer cavity comprises means for introducing a heat transfer gas which is a composition of at least two gases.

31. The cooling head of claim 28, wherein the heat exchanger support ring is close fit to the heat exchanger, and the flange is close fit to the heat exchanger support ting.

32. The cooling head of claim 28, wherein the outer diameter of the heat transfer cavity is greater than the inner diameter of the heat transfer cavity by 0.020 to 0.060 inches.

33. The cooling head of claim 27, wherein the minimum contact structure between the heat exchanger support ring and the heat exchanger consists of three to six contact regions.

34. The cooling head of claim 27, wherein the flange engages the heat exchanger support ring at three contact regions on the top of the flange and at three contact regions on the outside diameter of the flange.

35. The cooling head of claim 27, further comprising an outer housing surrounding the heat exchanger, wherein a space between the outer surface of the heat exchanger and the housing is substantially filled with an insulation material.

36. The cooling head of claim 35, further comprising an electrical resistance heater attached to the inner surface of the outer housing.

* * * * *

UNITED STATES PATENT AND TRADEMARK OFFICE
CERTIFICATE OF CORRECTION

PATENT NO. : 5,484,204
DATED : January 16, 1996
INVENTOR(S) : Robert L. DANLEY

It is certified that error appears in the above-identified patent and that said Letters Patent is hereby corrected as shown below:

On the title page, item [75] should read

Inventor: Robert L. DANLEY

Signed and Sealed this

Eighth Day of April, 1997

Attest:

BRUCE LEHMAN

Attesting Officer     Commissioner of Patents and Trademarks